(12) United States Patent
Iijima et al.

(10) Patent No.: US 9,282,903 B2
(45) Date of Patent: Mar. 15, 2016

(54) DEVICE FOR MEASURING BIOLOGICAL INFORMATION

(75) Inventors: Yoshitaka Iijima, Nagano (JP);
 Shigemitsu Tanaka, Nagano (JP);
 Yoshihiro Hidai, Nagano (JP)

(73) Assignee: Seiko Epson Corporation, Tokyo (JP)

( * ) Notice: Subject to any disclaimer, the term of this patent is extended or adjusted under 35 U.S.C. 154(b) by 429 days.

(21) Appl. No.: 12/950,374

(22) Filed: Nov. 19, 2010

(65) Prior Publication Data
US 2011/0125037 A1  May 26, 2011

(30) Foreign Application Priority Data
Nov. 20, 2009 (JP) ................ 2009-264684

(51) Int. Cl.
 *A61B 5/02* (2006.01)
 *A61B 5/024* (2006.01)
 *A61B 5/00* (2006.01)

(52) U.S. Cl.
 CPC ............. *A61B 5/02438* (2013.01); *A61B 5/681* (2013.01)

(58) Field of Classification Search
 CPC .......................... A61B 5/02438; A61B 5/681
 USPC ................................................ 600/500–507
 See application file for complete search history.

(56) References Cited

U.S. PATENT DOCUMENTS

| 4,901,733 A | * | 2/1990 | Kaida et al. ................. 600/500 |
| 6,527,726 B2 | * | 3/2003 | Goto et al. ................... 600/485 |
| 2004/0186387 A1 | | 9/2004 | Kosuda et al. |
| 2005/0049514 A1 | * | 3/2005 | Iwamiya et al. ............ 600/503 |
| 2005/0075553 A1 | * | 4/2005 | Sakai et al. ................. 600/372 |

FOREIGN PATENT DOCUMENTS

| JP | 04-049819 U1 | 4/1992 |
| JP | 11-235320 A | 8/1999 |
| JP | 2004-298606 A | 10/2004 |
| JP | 2005-127844 A | 5/2005 |
| JP | 3741148 B2 | 11/2005 |

* cited by examiner

*Primary Examiner* — Patricia Mallari
*Assistant Examiner* — Tiffany Weston
(74) *Attorney, Agent, or Firm* — Global IP Counselors, LLP (57) ABSTRACT

A device for measuring biological information by being worn on a person includes a sensor unit subjected to measure biological information, a device main unit provided with a concavity and subjected to accommodate the sensor unit, and a holding unit supported on one side by the sensor unit and on the other side by the device main unit; wherein the holding unit is elastic and has a space on one side of the concavity to hold the sensor unit so that at least part of the sensor unit extends outside from the device main unit, and wherein the sensor unit is displaced relative to the device main unit by elastic deformation in accordance with an external force applied to the sensor unit.

12 Claims, 5 Drawing Sheets

DEVICE FOR MEASURING BIOLOGICAL INFORMATION

BACKGROUND

1. Technical Field

The present invention relates to a device for measuring biological information using a biological information sensor.

2. Related Art

With the rise of health-consciousness and an increase in the number of people exercising in recent years, the frequency of disabilities or other accidents due to excessive exercise has increased. There is therefore an increasing need for a device that can readily measure a pulse, blood pressure, and other biological information and that should secure peace of mind and security for an individual.

As a device designed to fulfill this need, a pulse measuring device (referred to hereafter as a biological information measuring device) provided with a wristwatch-shaped device main unit and a wristband for wearing the device main unit on the arm, and used by being worn on the arm of a user is disclosed in Patent Document 1.

PRIOR ART DOCUMENTS

Patent Documents

[Patent Document 1] Japanese Laid-open Patent Application No. 2004-298606 (FIGS. 1 and 2)

DISCLOSURE OF THE INVENTION

Problems to Be Solved by the Invention

In the biological information measuring device of Patent Document 1, a pulse wave sensor (referred to hereafter as a sensor unit) is affixed to the underside cover of the device main unit, and biological information (pulse) from a wrist of a user is measured using the sensor unit by wearing the device main unit on the wrist of the user.

Measurements can thereby be taken under stable conditions by the biological information measuring device, and the biological information can be measured accurately because there is no change in the state of contact between the wrist and the sensor unit in the biological information measurements taken during rest when the wrist of the user remains substantially immovable.

However, in biological information measurements taken using a biological information measuring device during exercise or in other situations in which movement of the wrist of the user is substantial, the state of contact between the wrist and the sensor unit affixed to the device main unit tends to be frequently changed by the device main unit shifting, tilting in the thickness direction (referred to hereafter simply as "tilting"), and undergoing other changes induced by the wrist movement, creating concern that the biological information measurements may be taken under unstable conditions and that it may be difficult to accurately measure biological information.

SUMMARY

The present invention, which is aimed at solving the aforementioned problem at least partially, can be implemented as the following aspects or application examples.

APPLICATION EXAMPLE 1

A device according to the present application example is a device for measuring biological information by being worn on a person, the device comprising a sensor unit for measuring biological information, a device main unit provided with a concavity for accommodating the sensor unit, and a holding unit supported on one side by the sensor unit and on the other side by the device main unit, wherein the holding unit is elastic and has a space on one side of the concavity to hold the sensor unit so that at least part of the sensor unit extends outside from the device main unit, and wherein the sensor unit is displaced relative to the device main unit by elastic deformation in accordance with an external force applied to the sensor unit.

In this device, the holding unit has a space on one side of the concavity to hold the sensor unit so that at least part of the sensor unit extends outside from the device main unit, and the sensor unit is displaced relative to the device main unit by elastic deformation in accordance with an external force applied to the sensor unit.

The sensor unit of the device is therefore displaced so as to be forced into the concavity in the device main unit when, for example, the device is used by being worn on a wrist of a user.

The displacement causes the sensor unit of the device to be pressed against the wrist by the elasticity (flexibility) of the holding unit, and the external force applied to the sensor unit by the device main unit shifting, tilting, or undergoing other changes caused by the movement of the wrist is absorbed and reduced by the elastic deformation of the holding unit during exercise (for example, walking, running, stretching, sports, and the like) or the like in which movement of the wrist is substantial, making it possible to reduce the movement (shifting and tilting) that follows the device main unit of the sensor unit.

It is thereby possible to make it less likely than in the past that the state of contact between the sensor unit of the device and the wrist will change during an exercise in which the user makes large movements with their wrist.

As a result, biological information can be accurately measured because biological information measurements can be made under stable conditions even during an exercise in which the user makes large movements with their wrist, which is a condition under which accurate biological information measurements have been difficult to accomplish in the past.

APPLICATION EXAMPLE 2

In the device according to this application example, it is preferable that the sensor unit be provided with a light sensor.

Because the sensor unit is provided with a light sensor, the device can thereby accurately measure, for example, a pulse as biological information based on the sensor characteristics.

In addition, the sensor unit is pressed against the wrist by the holding unit, and good contact is maintained between the sensor unit and the wrist even during exercise or the like in which the user makes large movements with their wrist when, for example, the sensor unit of the device is used by being worn on the wrist of the user.

The device therefore inhibits outside light, which may be the cause of measurement noise, from entering the sensor unit provided with a light sensor, and is appropriately configured for the use of the light sensor.

APPLICATION EXAMPLE 3

In the device according to this application example, it is preferable that the device be configured so as to be able to be worn on a person's wrist.

The device is thus configured to be able to be worn on a person's wrist, and is therefore of a form amenable to being worn as a wristwatch. Reluctance toward wearing the device can be reduced and the device can be worn daily or for longer periods of time than in cases in which the device is worn on the chest or an ear, for example.

APPLICATION EXAMPLE 4

In the device according to this application example, the sensor unit and the holding unit are preferably made waterproof, and the interior of the device main unit is preferably sealed airtight.

The sensor unit and the holding unit of the device are thus made waterproof and the interior of the device main unit is sealed airtight, making it possible to prevent malfunctions from occurring inside the device main unit as a result of water entering through the sensor unit and the holding unit.

In addition, the sensor unit is displaced so as to be forced into the concavity of the device main unit by external pressure applied when the device is worn in cases in which, for example, the device is used by being worn on the wrist of the user.

At this time, the pressure inside the device main unit increases because the air inside the unit is compressed. The pressure acts as a reaction force on the sensor unit and the holding unit, whereby pressure at or above the elastic force of the holding unit is applied to the wrist of the user.

As a result, biological information measurements can be made under more stable conditions, and the biological information can therefore be measured more accurately by the device.

APPLICATION EXAMPLE 5

The device according to Application Example 4 preferably has an airflow unit capable of providing airflow between the interior of the device main unit and the outside air.

The device is thereby provided with an airflow unit capable of creating airflow between the interior of the device main unit and the outside air. The pressure difference between the interior of the device main unit and the outside air generated during movement or the like associated with variation in elevation can be resolved by providing airflow with the aid of the airflow unit.

As a result, adequate pushing pressure is consistently applied to the wrist of the user by the airflow unit without any effect from the ambient air pressure and the like when, for example, the sensor unit of the device is used by being worn on the wrist of the user.

Accordingly, it is possible for biological information measurements to be made under consistently stable conditions, and therefore for the biological information to be measured consistently and accurately by the device.

APPLICATION EXAMPLE 6

The device according to Application Example 5 is preferably configured so that the airflow unit is provided with a threaded section and that the airflow or sealing is performed by advancing or retracting the threaded section in accompaniment with rotation.

The device is thereby configured so that the airflow unit is provided with a threaded section and that airflow or sealing is performed by advancing or retracting the threaded section in accompaniment with rotation, making it easier to provide airflow between the interior of the device main unit and the outside air or to seal the interior of the device main unit merely by rotating the threaded section.

DESCRIPTION OF EXEMPLARY EMBODIMENTS

Figure 1:
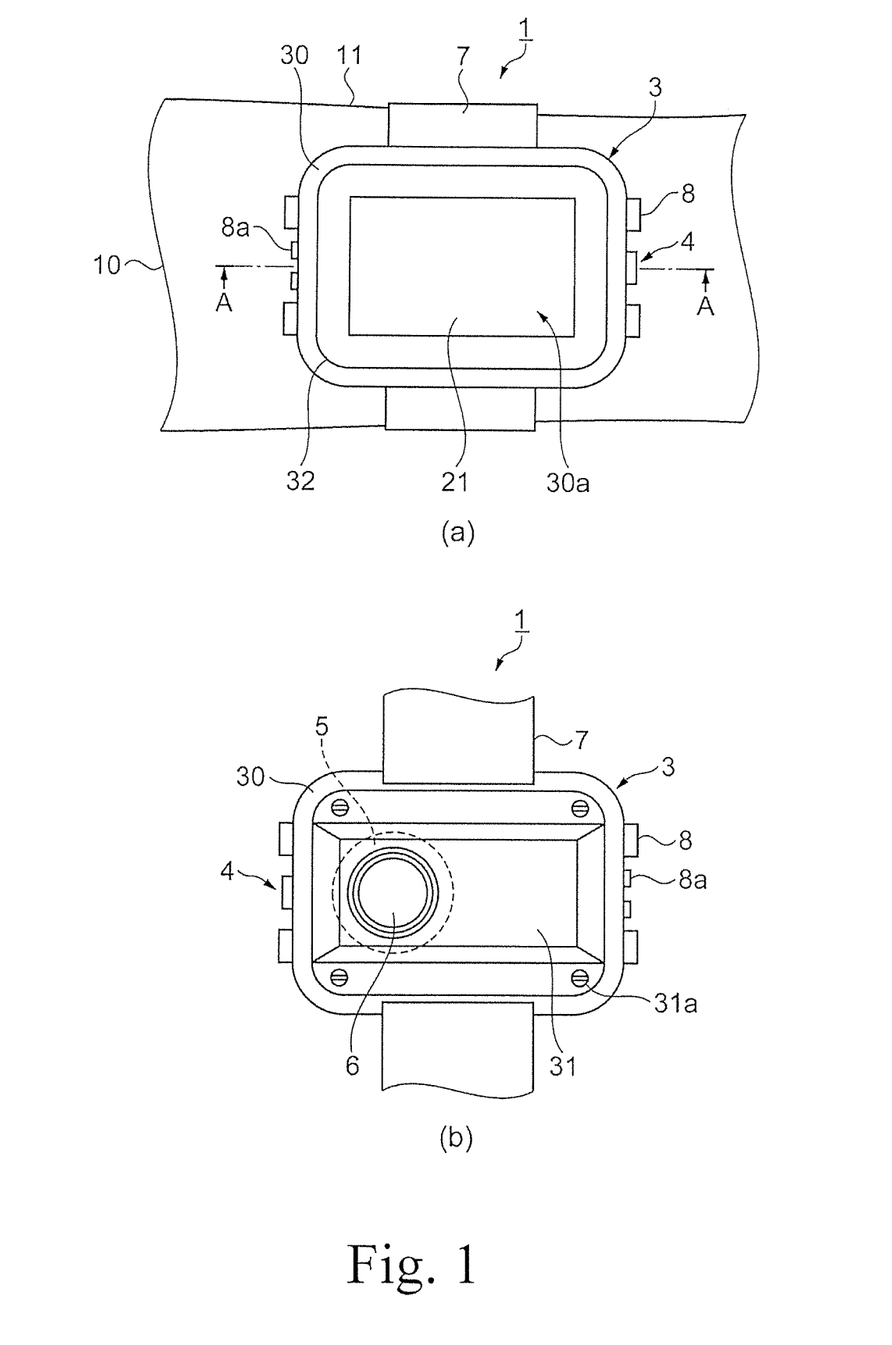
FIG. 1 is a schematic external view showing the external configuration of a pulse monitor according to the present embodiment.
Figure 2:
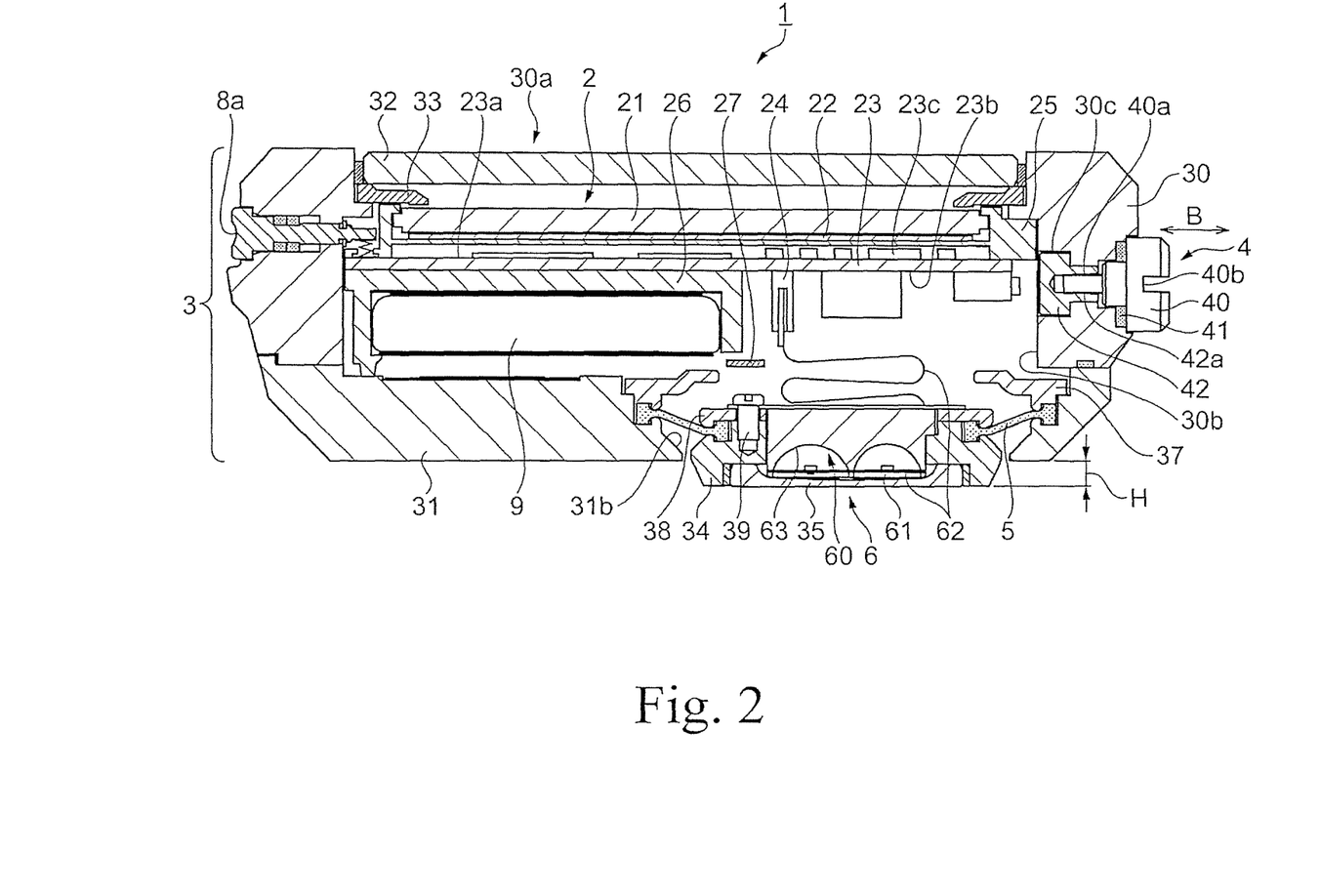
FIG. 2 is a cross-sectional view along line A-A of FIG. 1(a)

The present invention will now be described based on the drawings with reference to specific embodiments.
Embodiments FIG. 1 is a schematic external view showing the external configuration of a pulse monitor as a device according to the present embodiment. FIG. 1(a) is a plan view as seen from the side of the data display window section, and FIG. 1(b) is a plan view as seen from the side of the underside cover. FIG. 2 is a cross-sectional view along line A-A of FIG. 1(a). The data display is omitted in FIG. 1(a).

A pulse monitor 1 is formed in the shape of a wristwatch, can be worn on a person's arm 10, and is configured so as to be worn on a wrist 11, as shown in FIGS. 1 and 2.

The pulse monitor 1 comprises a pulse sensor unit 6 as a sensor unit for measuring a pulse as biological information, a head unit 3 as a device main unit, a pair of wristbands 7 attached to the head unit 3 and used for wearing the head unit 3 on the wrist 11, and a holding unit 5 supported on one side by the pulse sensor unit 6 and on the other side by the head unit 3.

The head unit 3 is provided with a case 30, a module 2, an underside cover 31, and underside cover setscrews 31a. A nylon-based resin or other material not amenable to cracking is used for the case 30 and the underside cover 31.

A concavity 30b is formed in the case 30 on the side facing the underside cover 31, the module 2 is accommodated in the concavity 30b, and the underside cover 31 is fixed in place by the metallic underside cover setscrews 31a so that the concavity 30b is covered by the underside cover 31.

A data display window unit 30a for displaying pulse measurement data and the like is formed in the case 30 on the side opposite from the underside cover 31, and a display panel 21 for displaying pulse measurement data and the like is constructed to be visible through the data display window unit 30a.

A cover body 32 formed from a transparent resin, transparent glass, or the like is also inset into the data display window unit 30a, and the display panel 21 of the module 2 is protected by the cover body 32. A frame-shaped accessory panel 33 on which the functions of operating buttons 8 (described hereinafter) are printed is disposed on the lower part of the external periphery of the cover body 32.

The case 30 is provided with a plurality of operating buttons 8 for inputting a variety of commands, such as switching on the illuminating light or changing modes from a pulse measurement mode for displaying pulse measurement data to a normal mode for displaying the current time and the like, or to a time-setting mode for setting the time.

In addition, the case 30 is provided with a pair of charging terminals 8a for use when charging a battery 9, which is the power source for the pulse monitor 1.

A through-hole 31b that passes through the underside cover 31 in the thickness direction is formed in the cover, and the hole functions as a concavity in the head unit 3 for accommodating the pulse sensor unit 6 together with the concavity 30b in the case 30.

The pulse sensor unit 6 is shaped roughly as a discoid in plan view. In the pulse sensor unit 6, a pulse sensor 60 is incorporated into a sensor frame 34 in which the cover body 35 formed from a transparent glass or the like is inset, and the sensor is fixed in place by a screw 39 via a sensor retainer 38 or the like.

Titanium or another metal material having minimal skin irritation is used for the sensor frame 34 pressed against the wrist 11 of the user. The use of a metal material provides the sensor frame 34 with a grounding connection to the person.

The portion of the pulse sensor unit 6 that is exposed to the outside is made waterproof by attaching the holding unit 5 (described hereinafter).

The pulse sensor 60 is a light sensor provided with a sensor case 61, a sensor board 62 on which a lightemitting element and a light-receiving element are mounted, and a light-collecting mirror 63.

The sensor board 62 is a flexible board obtained using a polyimide-based resin or the like, and the board is connected to a connector 24 of the module 2 (described hereinafter).

In the pulse sensor 60, light emitted by an LED (Light Emitting Diode) or other lightemitting element toward the wrist 11 of the user and reflected from the blood vessels of the wrist 11 toward the wrist 11 is concentrated by the light-collecting mirror 63 and received by a photodiode or other light-receiving element.

In the process, the pulse sensor 60 uses the differences in the reflection ratio of the light during expansion and contraction of the blood vessels to measure the pulse of the user.

Accordingly, the pulse sensor unit 6 is preferably pressed against the wrist 11, and more preferably is attached closely to the wrist 11, so that outside light, which is the source of measurement noise, is not received by the light-receiving element of the pulse sensor 60.

The holding unit 5 is elastic and is formed into a broad ring in plan view (refer to FIG. 1(b)).

The edge part along the internal periphery of the holding unit 5 is formed into a substantial O-ring, is compressed between the sensor frame 34 of the pulse sensor unit 6 and the sensor retainer 38, and is supported in a pinched state. The edge part along the external periphery of the holding unit 5 is similarly formed into a substantial O-ring, is compressed between the underside cover 31 and a holding unit retainer 37, and is supported in a pinched state.

The space between the edge part along the internal periphery of the holding unit 5 and the edge part along the external periphery of the unit is shaped at an incline in an outwardly facing bowl shape to support the pulse sensor unit 6 so that at least part of the pulse sensor unit 6 extends outside (toward the wrist 11) from the underside cover 31.

The amount H by which the pulse sensor unit 6 extends beyond the underside cover 31 is preferably kept at about 1.5 mm in order to secure appropriate pushing pressure against the wrist 11 and to reduce movement that follows the head unit 3 of the pulse sensor unit 6.

The pulse sensor unit 6 on the pulse monitor 1 is thereby pressed with appropriate pushing pressure against the wrist 11 by the elastic force of the holding unit 5 when the pulse monitor 1 is worn on the wrist 11.

Nitrile butadiene rubber (NBR) or another type of synthetic rubber commonly used as a waterproof packing for wristwatches and the like is used in the holding unit 5, and the holding unit 5 is made waterproof together with the pulse sensor unit 6.

Additional features of the holding unit 5 are that an increase in hardness at lower temperatures is prevented and the temperature dependence of the elastic force is reduced by using a fluorine-based additive.

An elastomer other than the aforementioned synthetic rubber may be used for the holding unit 5. The operation of the holding unit 5 will now be described in detail.

In the pulse monitor 1, a sealing member such as a waterproof packing is interposed between the case 30 and the components incorporated in the case 30, and the interior of the head unit 3 is sealed airtight by using the holding unit 5 to waterproof or otherwise seal the space between the through-hole 31b in the underside cover 31 and the pulse sensor unit 6.

In addition, the case 30 of the pulse monitor 1 is provided with an airflow unit 4 capable of providing airflow between the interior of the head unit 3, which is sealed airtight, and the outside air.

The airflow unit 4 is provided with a threaded pin 40 having a threaded section 40a (male screw), a washer 42 having a threaded section 42a (female screw), and a gasket 41.

In the airflow unit 4, the metallic washer 42 is inserted from the concavity 30b into a stepped through-hole 30c provided in a radial direction of the case 30. The threaded pin 40 with the incorporated gasket 41 formed in a ring shape using nitrile butadiene rubber or the like is inserted into the stepped through-hole 30c from outside of the case 30 in the airflow unit 4, and the threaded section 40a of the threaded pin 40 and the threaded section 42a of the washer 42 are threadably joined together.

The gasket 41 is compressed and restored (released from compression) between the threaded pin 40 and the case 30 in the airflow unit 4 by advancing (moving) the threaded pin 40 in the direction of arrow B in accompaniment with rotation, whereby airflow is provided between the interior of the head unit 3 and the outside air, and the interior of the head unit 3 is sealed (cut off from the outside air).

A straight slot 40b into which a coin or the like can be inserted is formed in the head section of the threaded pin 40. Part of the washer 42 and the portion of the stepped through-hole 30c in which the washer is accommodated are fashioned into an irregular shape or are otherwise machined to provide a rotation stop and to prevent the washer 42 from rotating in concert with the rotation of the threaded pin 40.

Movement of the washer 42 into the case 30 that accompanies rotation of the threaded pin 40 in the loosening direction is prevented as a result of the module 2 acting as a stopper, the washer 42 being press-fitted into the stepped through-hole 30c by interference, or the like.

The module 2 is provided with the display panel 21, an illuminating EL (electroluminescence) panel 22, a circuit board 23, a panel frame 25, a circuit case 26, a circuit retainer 27, and the battery 9, as shown in FIG. 2.

A panel frame 25 for positioning the display panel 21, the EL panel 22, and the like is disposed on one side 23a of the circuit board 23, and the circuit case 26 for positioning the battery 9 and the like is disposed on the other side 23b of the circuit board.

The layered panel frame 25, circuit board 23, and circuit case 26 are integrated together by disposing the main unit of the board-shaped circuit retainer 27 on the side of the circuit board case 26 facing the underside cover 31, and locking a plurality of arm sections (not shown) to the lateral surface of the panel frame 25. The arm sections extend from the external periphery of the main unit of the circuit retainer 27 along the lateral surface of the circuit case 26, and stretch all the way to the panel frame 25.

The layered panel frame 25, circuit board 23, circuit case 26, and circuit retainer 27 may be integrated together by using setscrews.

A board or the like based on an epoxy resin reinforced with glass fiber can be used for the circuit board 23, and a wiring pattern formed of copper foil or the like is formed on both surfaces. In addition, polycarbonate or another resin can be used for the panel frame 25 and the circuit case 26, and a stainless steel sheet or other metal sheet can be used for the circuit retainer 27.

An element 23c that constitutes a circuit for driving the pulse sensor 60 and measuring a pulse, a circuit for driving the display panel 21, a circuit for controlling the other circuits, and the like are mounted on the circuit board 23.

An electrode for connecting with the display panel 21 is formed on one side 23a of the circuit board 23, and conduction with the electrode of the display panel 21 is provided via a connector (not shown).

A liquid crystal panel or other display member is used for the display panel 21, and the display panel displays the pulse rate and other pulse measurement data, the current time and other time information, and the like according to each mode.

The EL panel 22 is disposed between the display panel 21 and the panel frame 25 and is connected to the circuit board 23, whereby lighting is provided by the operation of predetermined operating buttons 8 by the user, and the display panel 21 is illuminated.

A connector 24 connected to the sensor board 62 of the pulse sensor 60 is disposed on the other surface 23b of the circuit board 23. The distal section of the sensor board 62 is inserted into the insertion section of the connector 24 to electrically connect the circuit board 23 and the sensor board 62.

The sensor board 62 is thereby electrically connected to the circuit for driving the pulse sensor 60 and measuring a pulse.

The sensor board 62 is formed with a length that makes it easy to move the board in and out of the connector 24 in a state in which the pulse sensor unit 6 is attached to the underside cover 31, and can be accommodated so as to be folded when the underside cover 31 is attached to the case 30.

A button-type lithium rechargeable secondary cell battery is used for the battery 9 positioned in the circuit case 26. The terminals of both poles of the battery 9 are connected to the circuit board 23, and power is supplied to the circuit that controls the power source.

The power is converted or otherwise manipulated by the control circuit to obtain a predetermined voltage, and the voltage is supplied to the circuits to operate the circuit for driving the pulse sensor 60 and detecting a pulse, the circuit for driving the display panel 21, the circuit for controlling the other circuits, and the like.

The battery 9 is charged via a pair of charging terminals 8a made conductive with the circuit board 23 by a coil spring or other conduction member.

A primary cell battery for which charging is unnecessary may be used for the battery 9.

The operation of the holding unit 5 will now be described in detail.

Figure 3:
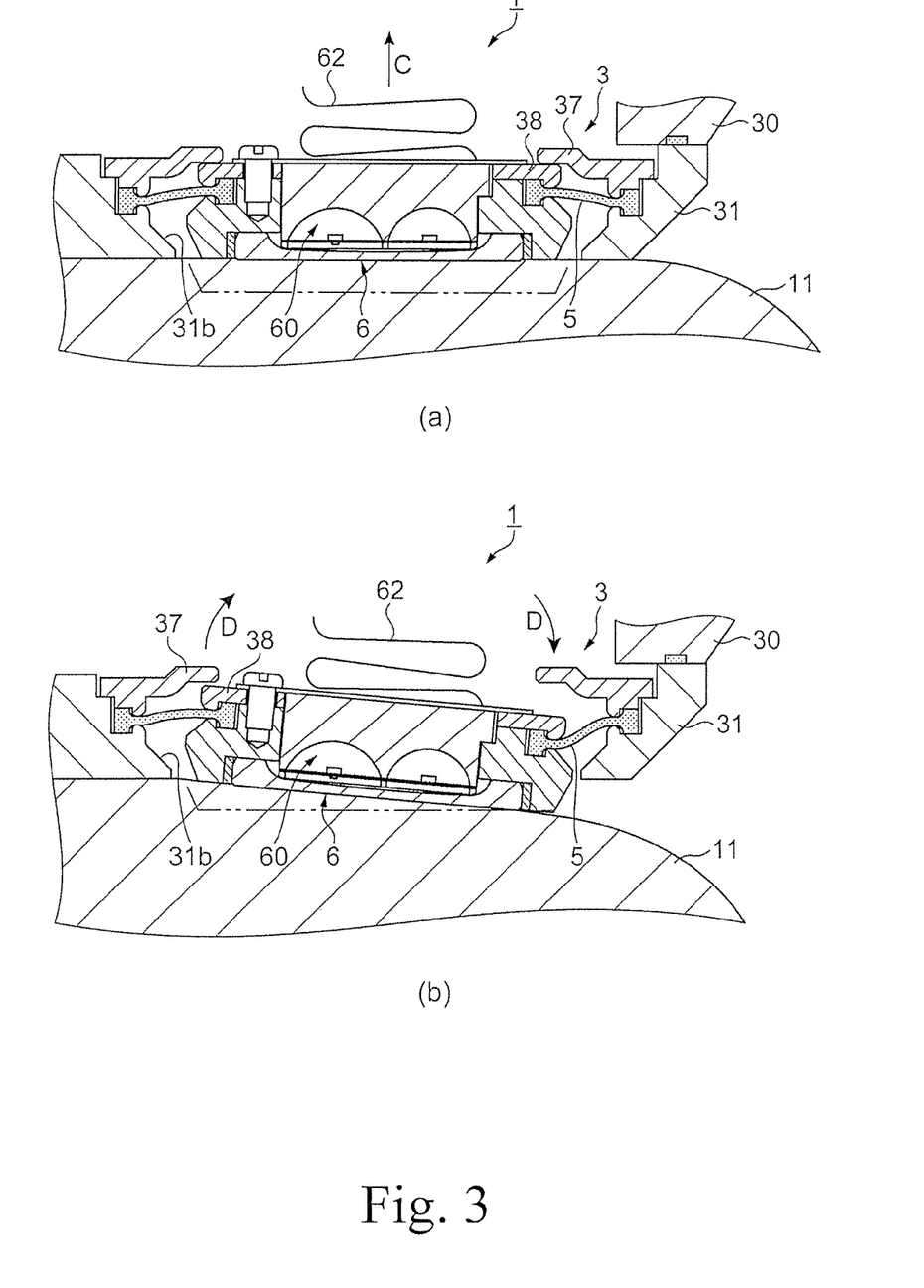
FIG. 3 is a schematic partial cross-sectional view showing a state in which the pulse monitor is worn on a wrist.

FIG. 3 is a schematic partial cross-sectional view showing a state in which the pulse monitor is worn on a wrist. FIG. 3(a) is a cross-sectional view showing a state in which the head unit is closely attached to the wrist, and FIG. 3(b) is a cross-sectional view showing a state in which the head unit is partially separated from the wrist. The dashed-two-dotted line in the drawing shows the main portion of the pulse sensor unit before displacement.

The pulse sensor unit 6 of the pulse monitor 1 is pressed against the wrist 11 when worn on the wrist 11, as shown in FIG. 3.

Specifically, the holding unit 5 of the pulse monitor 1 is elastically deformed by an external force applied by tightly wrapping the wristband 7 (refer to FIG. 1) around the wrist 11 when the head unit 3 is positioned on the flat part of the wrist 11, and the pulse sensor unit 6 is shifted (displaced) roughly parallel to the direction of arrow C so as to be forced into the through-hole 31b of the underside cover 31, as shown in FIG. 3(a).

The pulse sensor unit 6 in the pulse monitor 1 is pressed against and closely attached to the wrist 11 by the elastic force or the like of the holding unit 5.

The pulse monitor 1 is thereby held in a state in which the connecting state between the pulse sensor unit 6 and the wrist 11 is stable.

However, the wrist 11 sometimes moves as a result of exercise or the like, causing the head 3 of the pulse monitor 1 to move away from the flat part of the wrist 11 or to be tilted in the thickness direction, separating part of the head unit 3 from the wrist 11, as shown in FIG. 3(b).

In this case as well, the holding unit 5 is flexibly deformed in accordance with the movement of the head unit 3, and the pulse sensor unit 6 is displaced in the direction of arrow D in accompaniment with the rotation of the pulse sensor in the thickness direction in relation to the head unit 3, whereby the pulse monitor 1 is kept in a state in which the pulse sensor unit 6 is pressed against and closely attached to the wrist 11.

The pulse monitor 1 is thereby held in a state in which the pulse sensor unit 6 and the wrist 11 are kept in stable contact even when part of the head unit 3 is separated from the wrist 11.

That is, in the pulse monitor 1, the external force applied to the pulse sensor unit 6 by the head unit 3 shifting, tilting, or undergoing other changes caused by the movement of the wrist 11 is absorbed and reduced by the elastic deformation of the holding unit 5, and movement (lifting away from the wrist 11) of the pulse sensor unit 6 that follows the head unit 3 is reduced.

The amount of displacement of the pulse sensor unit 6 is reduced by the pressing of the sensor retainer 38 against the holding unit retainer 37 to avoid interference between the pulse sensor unit 6 and other components.

The pushing pressure of the pulse sensor unit 6 against the wrist 11 will now be described.

The pushing pressure of the pulse sensor unit 6 is related to the output signal level of the pulse sensor 60 at the time of pulse measurement, and is preferably kept at or above about 0.5 N in order to obtain a predetermined output signal level (for example, the output signal of the pulse sensor 60 is kept at or above 1 V) in a stable manner.

In addition, the blood vessels in the wrist 11 are compressed when the pushing pressure of the pulse sensor unit 6 in the pulse monitor 1 exceeds about 3 N, blocking the blood flow, making a predetermined output signal level difficult to maintain and creating concern that accurate pulse measurements will be impossible to obtain.

For this reason, the pushing pressure of the pulse sensor unit 6 on the wrist 11 is preferably set within a range of about 0.5 N to about 3 N.

In addition, maintaining a substantially constant pushing pressure in the pulse sensor unit 6 regardless of the amount of displacement of the pulse sensor unit 6 is preferable for obtaining more-accurate pulse measurements.

Figure 4:
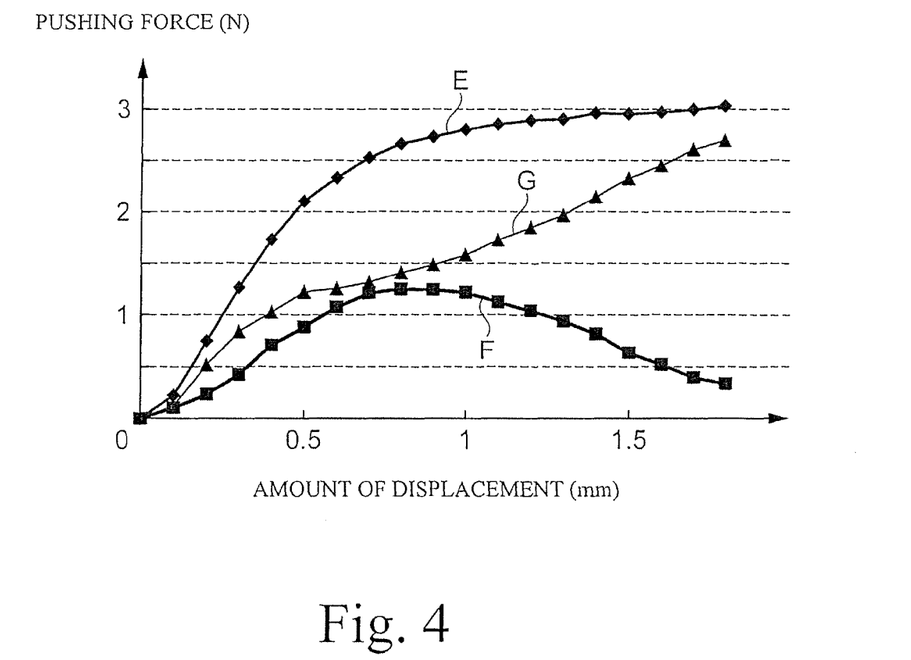
FIG. 4 is a graph showing an example of the relationship between the pushing pressure and the amount of displacement of the pulse sensor unit.

FIG. 4 is a graph showing an example of the relationship between the pushing pressure and the amount of displacement of the pulse sensor unit. The vertical axis shows the pushing pressure, and the horizontal axis shows the amount of displacement in the thickness direction (the direction of arrow C in FIG. 3).

Curve E in FIG. 4 expresses the pushing pressure of the pulse sensor unit 6, curve F expresses the elastic force of the holding unit 5, and curve G expresses the pressure inside the airtightly sealed head unit 3.

The pushing pressure (curve E) of the pulse sensor unit 6 is a value obtained by adding the pressure (curve G) inside the head unit 3 to the elastic force (curve F) of the holding unit 5, as shown in FIG. 4.

Depending on characteristics determined by the shape of the holding unit 5, the elastic force of the unit increases substantially proportionally to the amount of displacement until the amount of displacement reaches 0 mm to about 1 mm, and the elastic force gradually decreases thereafter.

In addition, the pressure inside the airtightly sealed head unit 3 increases substantially proportionally to the amount of displacement of the pulse sensor unit 6 forced into the throughhole 31*b* in the underside cover 31, due to the increase in the compression rate of the air in the interior.

The pushing pressure of the pulse sensor unit 6 is thereby set so as to compensate for the reduction in the elastic force of the holding unit 5 by increasing the pressure inside the head unit 3.

As a result, the pushing pressure of the pulse sensor unit 6 is securely kept at a substantially constant value (slightly less than 3 N) in a range (from slightly less than 1 mm to slightly more than 1.5 mm, for example) in which the amount of displacement of the pulse sensor unit 6 is assumed to vary during daily use.

In the pulse monitor 1 according to the present embodiment as described above, the holding unit 5 is elastic and has a space between the through-hole 31*b* of the underside cover 31 and the concavity 30*b* of the case 30 to hold the pulse sensor unit 6 so that at least part of the pulse sensor unit 6 extends outside (toward the wrist 11) from the underside cover 31.

The pulse sensor unit 6 in the pulse monitor 1 is displaced relative to the head unit 3 so as to be forced into the through-hole 31*b* of the underside cover 31 (into the concavity 30*b* of the case 30) by elastic deformation of the holding unit 5 in accordance with the external force applied to the pulse sensor unit 6.

The pulse sensor unit 6 is thereby pressed against and closely attached to the wrist 11 by the holding unit 5 when the pulse monitor 1 is used by being worn on the wrist 11 of the user.

The external force applied to the pulse sensor unit 6 of the pulse monitor 1 by the head unit 3 shifting, tilting, or undergoing other changes caused by the movement of the wrist 11 is absorbed and reduced by the elastic deformation of the holding unit 5 during exercise or the like in which movement of the wrist 11 is substantial.

As a result, the movement of the pulse sensor unit 6 that follows the head unit 3 is reduced, whereby lifting of the pulse sensor unit 6 away from the wrist 11 can be avoided.

It is thereby possible to make it less likely than in the past that the state of contact between the pulse sensor unit 6 of the pulse monitor 1 and the wrist 11 will change during exercise or in other situations in which movement of the wrist 11 of the user is substantial.

As a result, a pulse can be accurately measured by the pulse monitor 1 because pulse measurements can be made under stable conditions even during exercise or the like in which the user makes large movements with their wrist 11, which is a condition under which accurate pulse measurements were difficult to accomplish in the past.

In addition, a light sensor is used for the pulse sensor 60 of the pulse sensor unit 6, for which reason a pulse can be accurately measured by the pulse monitor 1 using the differences in the reflection ratio of light during expansion and contraction of the blood vessels in accordance with the characteristics of the light sensor.

Furthermore, the pulse sensor unit 6 is pressed against the wrist 11 by the holding unit 5, and good contact is maintained between the pulse sensor unit 6 and the wrist 11 even during exercise or the like in which the user makes large movements with their wrist 11 when the pulse sensor unit 6 of the pulse monitor 1 is used by being worn on the wrist 11 of the user.

The pulse monitor 1 therefore inhibits outside light, which may be the cause of measurement noise, from entering the pulse sensor unit 6 provided with the light sensor (pulse sensor 60), and is appropriately configured for the use of a light sensor.

The pulse monitor 1 is also configured to be able to be worn on the wrist 11 of a person's arm 10, and is therefore of a form amenable to being worn as a wristwatch. Reluctance toward wearing the monitor can be reduced compared with cases in which the monitor is worn on the chest or an ear, for example.

In addition, the pulse monitor 1 can be worn daily or for longer periods of time by the user because reluctance toward wearing the monitor can be reduced, as described above.

The pulse sensor unit 6 and the holding unit 5 of the pulse monitor 1 are also made waterproof and the interior of the head unit 3 is sealed airtight, making it possible to prevent malfunctions from occurring inside the head unit 3 as a result of water entering through the pulse sensor unit 6 and the holding unit 5.

In addition, the pulse sensor unit 6 is pressed on and displaced so as to be forced into the through-hole 31*b* of the underside cover 31 by external pressure applied when the pulse monitor 1 is worn in cases in which the monitor is used by being worn on the wrist 11 of the user.

At this time, the pressure inside the head unit 3 of the pulse monitor 1 increases because the air inside the unit is compressed. The pressure acts as a reaction force on the pulse sensor unit 6 and the holding unit 5, whereby a pushing pressure at or above the elastic force of the holding unit 5 is applied to the wrist 11 of the user.

The pressure inside the head unit 3 of the pulse monitor 1 can compensate for the reduction in the elastic force of the holding unit 5, and the pushing pressure on the pulse sensor unit 6 can be kept at a substantially constant value (slightly less than 3 N) in a range (from slightly less than 1 mm to slightly more than 1.5 mm, for example) in which the amount of displacement of the pulse sensor unit 6 is assumed to vary during daily use.

As a result, pulse measurements can be made under more stable conditions, and a pulse can therefore be measured more accurately by the pulse monitor 1.

The size of the pulse sensor unit 6 and the holding unit 5 is appropriately set with consideration for conditions such as the compression rate of the air inside the head unit 3 in accordance with the displacement of both units.

The pulse monitor 1 also has an airflow unit 4 capable of creating airflow between the interior of the head unit 3 and the outside air, for which reason the pressure difference between the interior of the head unit 3 and the outside air, which is brought about by variation in air pressure during movement (mountain climbing, travel, and the like) accompanied by factors such as variation in elevation or expansion and contraction of air accompanied by variation in temperature inside the head unit 3, can be resolved by providing airflow with the aid of the airflow unit 4.

As a result, adequate pushing pressure can be consistently applied to the wrist 11 of the user by the operation of the airflow unit 4 of the pulse monitor 1 without any effect from variations in the ambient air pressure, variations in the temperature inside the head unit 3, and other variations.

The pressure inside the head unit 3 increases in relative terms when, for example, the ambient air pressure decreases during mountain climbing or the like, causing the pulse sensor unit 6 of the pulse monitor 1 to press more than necessary against the wrist 11, blocking the blood flow in the wrist 11, making a predetermined output signal level difficult to obtain, and creating concern that accurate pulse measurements will be impossible to make.

At this time, airflow is created in the pulse monitor 1 between the interior of the head unit 3 and the outside air, and the pressure difference between the interior of the head unit 3 and the outside air is resolved by rotating the threaded pin 40 of the airflow unit 4 in the loosening direction.

The pushing pressure of the pulse sensor unit 6 in the pulse monitor 1 can thereby be kept within the appropriate range because the pressure inside the head unit 3 is reduced.

Accordingly, a pulse can be measured accurately by the pulse monitor 1 because pulse measurements can be made under stable conditions without blocking the blood flow in the wrist 11.

The pressure inside the head unit 3 becomes lower than the ambient pressure (state of negative pressure is established) when descending a mountain after airflow has been provided and the interior of the head unit 3 has been sealed at high altitude, creating concern that the pushing pressure of the pulse sensor unit 6 will decrease in a commensurate manner.

In response to this, airflow is reestablished by the airflow unit 4 of the pulse monitor 1, the pressure difference between the interior of the head unit 3 and the outside air is resolved, and the pushing pressure inside the head unit 3 is raised, whereby the pressure of the pulse sensor unit 6 can be kept within the appropriate range.

In addition, the airflow unit 4 of the pulse monitor 1 is provided with a threaded pin 40 having a threaded section 40a, and the gasket 41 is compressed or restored (released from compression) between the threaded pin 40 and the case 30 by advancing or retracting the threaded pin 40 (threaded section 40a), whereby airflow is provided between the interior of the head unit 3 and the outside air, or the interior of the head unit 3 is sealed.

It can therefore be made easier to seal the interior of the head unit 3 or to create airflow between the interior of the head unit 3 and the outside air merely by rotating the threaded pin 40 of the pulse monitor 1.

In addition, a straight slot 40b into which a coin or the like can be inserted is formed in the head section of the threaded pin 40, for which reason the airflow unit 4 of the pulse monitor 1 can be readily operated by rotating the threaded pin 40 using a coin at hand without using a special tool or the like.

Modifications

The present invention will now be described based on the drawings with reference to a modification of the aforementioned embodiment.

Figure 5:
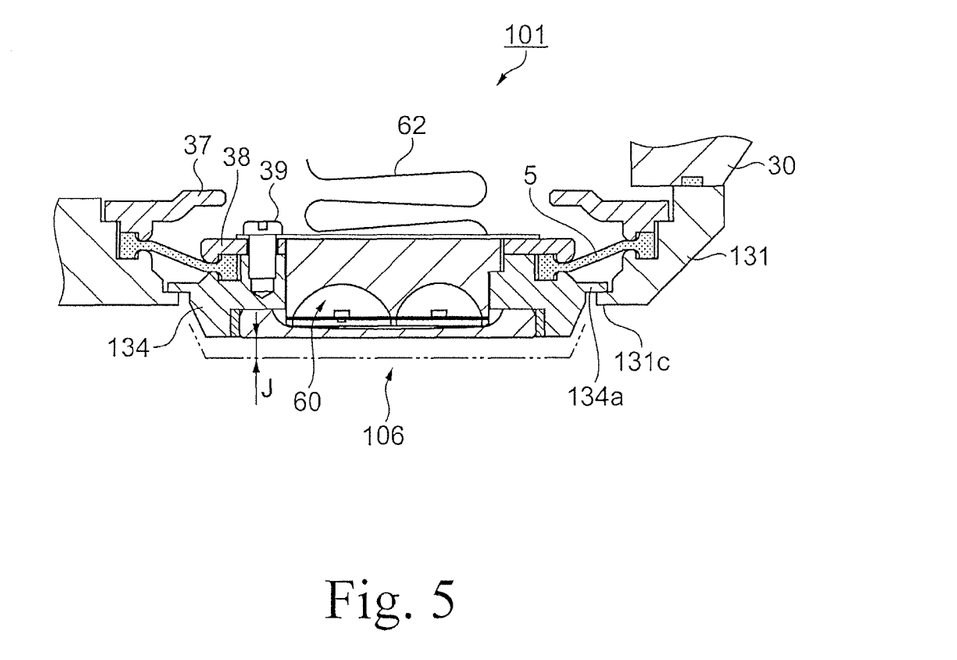
FIG. 5 is a schematic partial cross-sectional view of a pulse monitor according to a modification.

FIG. 5 is a schematic partial cross-sectional view of a pulse monitor according to the modification. The positions in cross section are the same as the positions in cross section in FIG. 2. In addition, the same symbols are attached and descriptions are omitted for portions in common with the aforementioned embodiment. The description will focus on the portions differing from the aforementioned embodiment.

In a pulse monitor 101 according to the modification, a radially extended flange section 134a of a pulse sensor unit 106 is formed on the lateral surface of the external periphery of a sensor frame 134 in the pulse sensor unit 106, as shown in FIG. 5.

In addition, a regulator 131c for controlling the amount of extension of the pulse sensor unit 106 from an underside cover 131 toward the outside is formed in the underside cover 131 so as to overlap the flange section 134a in plan view.

The pulse sensor unit 106 is held by the holding unit 5 so as to extend up to the position shown by the dashed-two-dotted line in FIG. 5 if the regulator 131c is not present.

That is, the flange section 134a is pressed against the regulator 131c, and the amount of extension of the pulse sensor unit 106 from the underside cover 131 toward the outside is controlled when the pulse sensor unit 106 is attached to the underside cover 131.

At the moment when the pulse sensor unit 106 is attached to the underside cover 131, the holding unit 5 is thereby elastically deformed (warped), the pulse sensor unit 106 is displaced by a displacement amount J from the position shown by the dashed-two-dotted line toward the case 30, and a pushing pressure is already generated in a quantity commensurate with the displacement amount J (also referred to hereinafter as "initial warp J").

Figure 6:
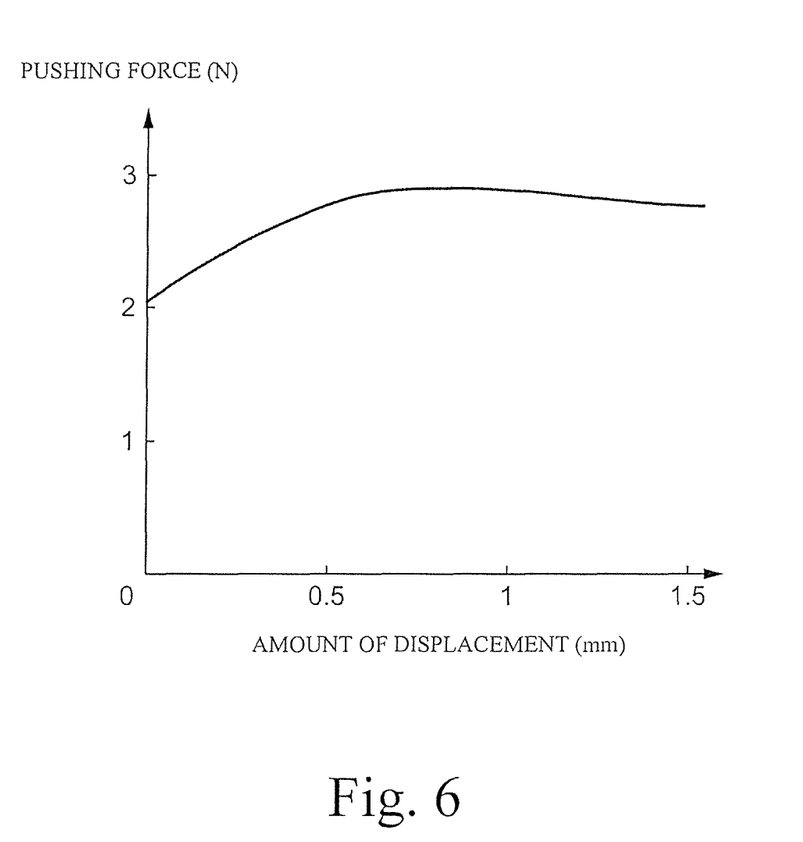
FIG. 6 is a graph showing an example of the relationship between the pushing pressure and the amount of displacement of a pulse sensor unit according to a modification.

Setting the initial warp J for the pulse monitor 101 allows adequate pushing pressure (from slightly more than 2 N to slightly less than 3 N) to be applied to the wrist 11 even when the amount of displacement of the pulse sensor unit 106 is small (at or below 0.5 mm, for example), as displayed in the graph in FIG. 6. The graph shows an example of the relationship between the amount of displacement and the pushing pressure of the pulse sensor unit.

A pulse can thereby be measured more accurately by the pulse monitor 101 because the pulse can be measured under more-stable conditions than in the aforementioned embodiment.

In addition, in the pulse monitor 101, the flange section 134a of the pulse sensor unit 106 is pressed against the regulator 131c, and a gap cannot be formed between the two components. Therefore, unlike in the aforementioned embodiment, ingress of debris and other foreign matter through the gap between the underside cover 131 and the pulse sensor unit 106 during storage or at other times can be prevented by forming the flange section 134a and the regulator 131c around the entire periphery of the pulse sensor unit 106.

Malfunctions due to ingress of debris and other foreign matter can thereby be prevented in the pulse monitor 101.

The device for measuring biological information was described with reference to a pulse monitor in the embodiment and modification above, but this description is not limiting, and the present invention can also be applied to a blood pressure monitor for measuring blood pressure as biological information, and to other monitors.

It is possible to increase the pushing pressure of the pulse sensor unit 6, 106 by pressing the pulse sensor unit 6, 106 toward the wrist 11 using a coil spring or other elastic member provided to the module 2, for example, to counter the decrease in the air compression rate inside the head unit 3 brought about by miniaturization and other changes to the pulse sensor unit 6, 106 and the holding unit 5.

The entire disclosure of Japanese Patent Application No. 2009-264684, filed Nov. 20, 2009 is expressly incorporated by reference herein.

What is claimed is:

1. A device for measuring biological information by being worn on a measured object, the device comprising:
   a sensor unit configured to measure biological information;
   a device main unit provided with a concavity accommodating the sensor unit in the concavity; and
   a holding unit supporting the sensor unit and the device main unit with a space therebetween, the holding unit being elastic,
   the holding unit including an inner periphery part, an outer periphery part with an outer periphery surface, and an inclining part,
   the inner periphery part being coupled to the sensor unit, the inner periphery part having an inner periphery surface, a first surface, and a second surface, the inner periphery surface defining an opening of the holding unit, the first surface and the second surface being opposite to each other such that the inner periphery surface is disposed between the first surface and the second surface, the opening penetrating through the holding unit from the first surface to the second surface, both of the first surface and the second surface contacting the sensor unit
   the outer periphery surface being coupled to the device main unit,
   the inclining part being disposed between the inner periphery part and the outer periphery part,
   a thickness of the inner periphery part and a thickness of the outer periphery part being greater than a thickness of the inclining part,
   the sensor unit being displaced relative to the device main unit by elastic deformation of the holding unit in accordance with an external force applied to the sensor unit.

2. The device of claim 1, wherein
   the sensor unit is provided with a light sensor.

3. The device of claim 1, wherein
   the device is configured so as to be worn on a person's wrist.

4. The device of claim 1, wherein
   the sensor unit and the holding unit are made waterproof.

5. The device of claim 4, further comprising an airflow unit configured to provide airflow between an interior of the device main unit and the outside air.

6. The device of claim 5, wherein
   the airflow unit includes a threaded section, and the airflow or sealing is performed by advancing or retracting the threaded section in accompaniment with rotation.

7. The device of claim 1, wherein
   the sensor unit is displaced relative to the device main unit in a displacement direction, and the thickness extending in the displacement direction of the internal periphery part and the thickness extending in the displacement direction of the outer periphery part are greater than the thickness extending in the displacement direction of the inclining part.

8. The device of claim 1, wherein
   the holding unit is integrated as a one piece, unitary member.

9. The device of claim 1, wherein
   the sensor unit includes a sensor retainer holding the holding unit,
   the device main unit includes a holding unit retainer protruding, toward the concavity, inward relative to the outer periphery surface of the holding unit, and
   the holding unit retainer is configured to contact the sensor retainer as the sensor unit is displaced relative to the device main unit.

10. The device of claim 9, wherein
    the sensor unit further includes a contact surface configured to contact the measured object,
    the sensor retainer is arranged closer to the contact surface than the holding unit retainer.

11. The device of claim 1, wherein
    the inner periphery part is compressed by contact with the sensor unit.

12. The device of claim 1, wherein
    the sensor unit includes a sensor flame and a sensor retainer that hold the holding unit, and
    the inner periphery part is disposed between the sensor flame and the sensor retainer such that the sensor flame contacts the first surface and the sensor retainer contacts the second surface.

* * * * *